US010568601B2

(12) United States Patent
Tkaczyk et al.

(10) Patent No.: US 10,568,601 B2
(45) Date of Patent: Feb. 25, 2020

(54) RADIOGRAPHY SYSTEM AND METHOD OF CONTROLLING RADIOGRAPHY SYSTEM THEREOF

(71) Applicant: GENERAL ELECTRIC COMPANY, Schenectady, NY (US)

(72) Inventors: John Eric Tkaczyk, Niskayuna, NY (US); Feng Pan, Niskayuna, NY (US); Jiajun Gu, ShangHai (CN); Zirong Zhai, ShangHai (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/124,691

(22) Filed: Sep. 7, 2018

(65) Prior Publication Data

US 2019/0076106 A1 Mar. 14, 2019

(30) Foreign Application Priority Data

Sep. 8, 2017 (CN) .......................... 2017 1 0805529

(51) Int. Cl.
*G01N 23/04* (2018.01)
*A61B 6/00* (2006.01)

(52) U.S. Cl.
CPC .................................. *A61B 6/5294* (2013.01)

(58) Field of Classification Search
CPC ....... A61B 6/5294; A61B 6/547; A61B 6/545; A61B 6/542; A61B 6/4405; A61B 6/4283;

(Continued)

(56) References Cited

U.S. PATENT DOCUMENTS 6,771,734 B2 * 8/2004 Hebecker ............. A61B 6/4405
378/8
7,581,884 B1 9/2009 Barnes et al.
(Continued)

FOREIGN PATENT DOCUMENTS

CN 101683271 B 3/2014
WO 2016029845 A1 3/2016

OTHER PUBLICATIONS

Zang et al., "CUDA Acceleration of 3D Dynamic Scene Reconstruction and 3D Motion Estimation for Motion Capture", IEEE 18th International Conference on Parallel and Distributed Systems, Dec. 17-19, 2012.

(Continued)

*Primary Examiner* — Kiho Kim
(74) *Attorney, Agent, or Firm* — Fletcher Yoder, P.C.

(57) ABSTRACT

A radiography system for imaging an object, comprises a radiation source located in a first side of the object for generating a plurality of beams; a detector located in a second side of the object for detecting the plurality of beams from the radiation source. The radiography system comprises a first sensor located in the first side of the object for obtaining an object related information and a second sensor disposed on the detector for obtaining a detector-position related information. The radiography system further comprises a controller configured to reconstruct a 3D scene based on the object related information obtained by the first sensor and the detector-position related information obtained by the second sensor and control an operation of at least one of the radiation source and the detector based on the reconstructed 3D scene. A method of controlling the radiography system is also disclosed.

20 Claims, 3 Drawing Sheets

(58) Field of Classification Search
CPC .............................. A61B 6/0407; A61B 6/54;
A61B 6/48; G01S 17/88
See application file for complete search history.

(56) References Cited

U.S. PATENT DOCUMENTS

| | | | |
|---|---|---|---|
| 9,649,080 B2* | 5/2017 | Kwak | A61B 6/4429 |
| 9,907,518 B2* | 3/2018 | Gooβen | A61B 6/0492 |
| 2013/0279646 A1 | 10/2013 | Koike et al. | |
| 2015/0228071 A1 | 8/2015 | Jockel et al. | |
| 2016/0089104 A1* | 3/2016 | Naito | A61B 6/588 |
| | | | 600/449 |
| 2016/0148398 A1* | 5/2016 | Takemoto | G06T 11/005 |
| | | | 378/63 |
| 2016/0174930 A1* | 6/2016 | Braun | A61B 34/20 |
| | | | 378/205 |
| 2016/0262713 A1 | 9/2016 | Flohr et al. | |
| 2018/0338742 A1* | 11/2018 | Singh | A61B 6/4464 |

OTHER PUBLICATIONS

Rodriguez et al., "Multimodal Calibration of Portable X-Ray Capture Systems for 3D Reconstruction", 2nd International Conference on 3D Vision, Dec. 8-11, 2014.
Gotardo et al., "Photogeometric Scene Flow for High-Detail Dynamic 3D Reconstruction", IEEE International Conference on Computer Vision, Dec. 7-13, 2015.
Albiol et al., "Geometrical Calibration of X-Ray Imaging With RGB Cameras for 3D Reconstruction", IEEE Transactions on Medical Imaging, vol. 35, Issue 8, pp. 1952-1961, Aug. 2016.

\* cited by examiner

RADIOGRAPHY SYSTEM AND METHOD OF CONTROLLING RADIOGRAPHY SYSTEM THEREOF

BACKGROUND

The present disclosure relates generally to a radiography system and a method of controlling the radiography system.

Radiography imaging systems are widely used in hospitals. The radiography imaging system comprises a radiation source and a detector. The radiation source generates a plurality of x-ray beams. An operator (expert technician) is required to operate the radiography imaging system for imaging a patient. A current operation workflow of the radiography imaging system comprises many manual operations by the operator for initializing an exposure period after positioning the patient relative to the radiation source and the detector. The operator's inaccurate visual estimation and/or a patient's motion occurring after positioning may result in unacceptable images. For example, some aspects of an anatomy of the patient may be missing from a projected field of view of the radiation source if the radiation source does not well align with the detector. The patient may move after the detector is well positioned relative to the patient but before the radiation source is actuated to acquire an image. All those reasons may affect the quality of the images. As such, retakes may be needed.

For example, to acquire of a chest x-ray image, the current workflow requires the operator (expert technician) to usher the patient to an x-ray detector of an imager in an examination room, adjust the detector and an x-ray tube of the radiation source to an appropriate height and adjust a setting of a collimator at same time. The technician expert then leaves the examination room and releases x-ray exposure. There are lots of manual operations in current workflow. The technical expert initiates the radiation source by inaccurate visual estimation. Thus, the technician expert may not narrow the field of view sufficiently. It would increase radiation dose to the patient. And, as the technician expert can't get a physiognomy information of the patient (such as a size or thickness of the patient) in current work flow, the technician expert can't reduce the amount of the radiation dose delivered to the patient. It may result in large dosages delivered to the patient or a long exposure time.

Thus, there is a need for a radiography imaging system and a method of controlling the radiography imaging system to address at least one of the above-mentioned problems.

BRIEF DESCRIPTION

In one embodiment, the present disclosure provides a radiography system for imaging an object. The radiography system comprises a radiation source located in a first side of the object for generating a plurality of beams; a detector located in a second side of the object for detecting the plurality of beams from the radiation source. The radiography system comprises a first sensor located in the first side of the object for obtaining an object related information and a second sensor disposed on the detector for obtaining a detector-position related information. The radiography system further comprises a controller configured to reconstruct a 3D scene based on the object related information obtained by the first sensor and the detector-position related information obtained by the second sensor and control an operation of at least one of the radiation source and the detector based on the reconstructed 3D scene.

In another embodiment, the present disclosure provides a method of controlling a radiography system. The radiography system comprises a radiation source and a detector for imaging an object. The method comprises obtaining an object related information by a first sensor located in a first side of the object; obtaining a detector-position related information by a second sensor disposed on the detector; and reconstructing a 3D scene based on the object related information obtained by the first sensor and the detector-position related information obtained by the second sensor and controlling an operation of at least one of the radiation source and the detector based on the reconstructed 3D scene.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Embodiments of the present disclosure will be described herein below with reference to the accompanying drawings. In the following description, well-known functions or constructions are not described in detail to avoid obscuring the disclosure in unnecessary detail.

Unless defined otherwise, technical and scientific terms used herein have the same meaning as is commonly understood by one of ordinary skill in the art to which this disclosure belongs. The terms "first", "second", "third" and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean either or all of the listed items. The use of "including," "comprising" or "having" and variations thereof herein are meant to encompass the items listed thereafter and equivalents thereof as well as additional items. In addition, the terms "connected" and "coupled" are not restricted to physical or mechanical connections or couplings, and can include electrical connections or couplings, whether direct or indirect.

Embodiments of the present disclosure may be described herein in terms of functional components and various processing steps. It should be appreciated that such functional components may be realized by any number of hardware, software, and/or firmware components configured to perform the specific functions. For example, an embodiment of the present disclosure may employ various integrated circuit components, e.g., memory elements, digital signal processing elements, logic elements, look-up tables, or the like, which may carry out a variety of functions of "controller" under the control of one or more microprocessors or other control devices. Moreover, the system described herein merely illustrates one exemplary embodiment.

Figure 1:
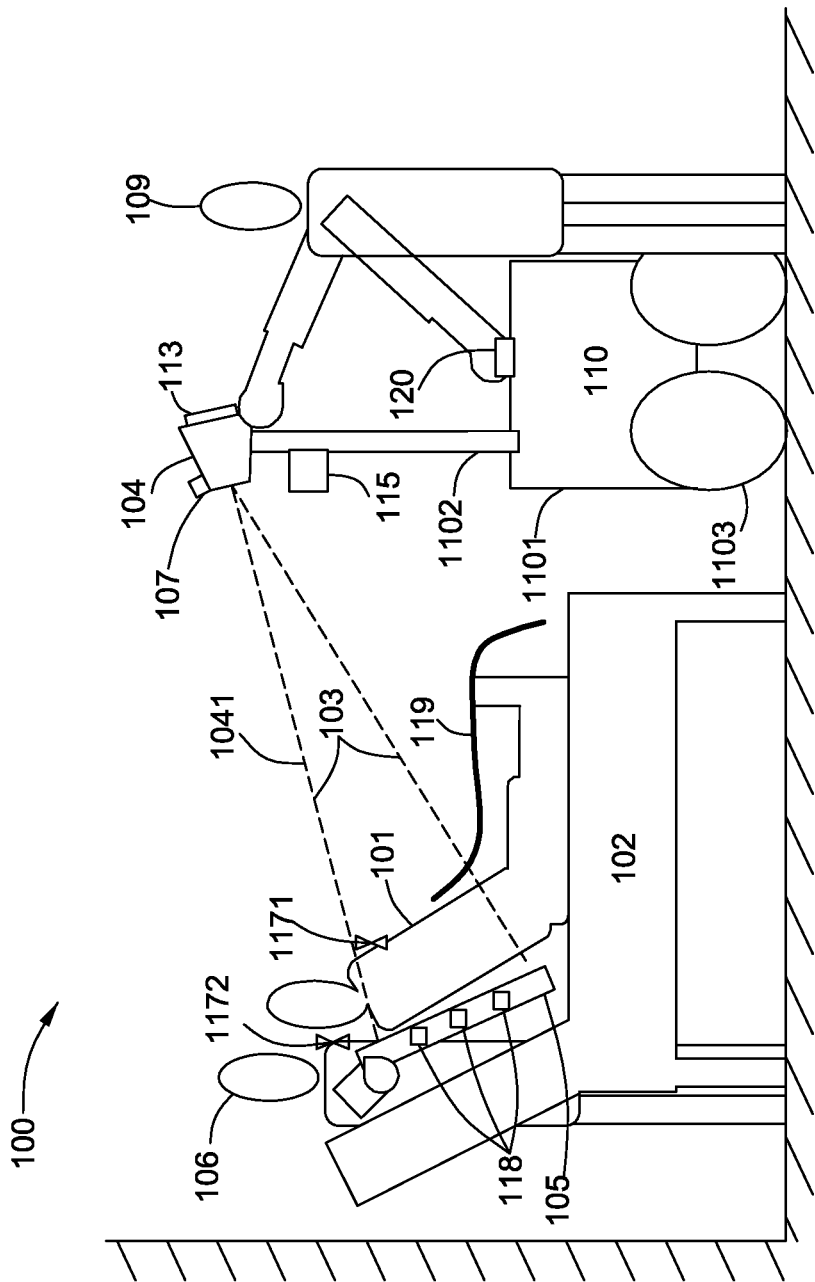
FIG. 1 is a schematic view of a radiography system in accordance with an embodiment of the present disclosure.

FIG. 1 is a schematic view of a radiography system 100 in accordance with an exemplary embodiment of the present disclosure. As shown in FIG. 1, the radiography system 100 comprises a radiation source 104 and a detector 105. The radiography system 100 is used for imaging an object 101.

The radiation source 104, also termed an x-ray tube, tube head, or generator, radiates a plurality of beams 1041, such as X-ray beams or Gamma ray beams toward the detector 105 and the object 101. The detector 105 can detect the plurality of beams 1041 that pass through the object 101. The object 101 may be a patient, an animal or other suitable objects. In some embodiments, the detector 105 is in a form of a pad. The detector 105 can receive the plurality of beams 1041 emanating from the radiation source 104. The detector 105 can produce electrical signals that respectively represent the beams passing through the object 101. The electrical signals are then consolidated into an array of digital values for forming an X-ray projection image. The detector 105 may be a movable detector, and also may be other type of detectors. In a specific embodiment, the detector 105 is a flat and portable digital detector.

In the exemplary embodiment, the radiography system 100 is a mobile radiography system. However, a fixed type radiography system may be used in other embodiments. The mobile radiography system 100 comprises a supporting device 110 for supporting the radiation source 104. The supporting device 110 comprises a transport frame 1101 and a vertical column 1102 mounted on the transport frame 1101. The radiation source 104 is coupled to a top end of the vertical column 1102. The radiation source 104 can move up and down on the vertical column 1102 to a desired height for acquiring an image on the portable detector 105. The radiation source 104 may rotate relative to the vertical column 1102 to any angle for aiming the object 101. Positioning of the radiation source 104 can be actuated by a motor drive mechanism (not shown) responding to control signals in the system controller 120 to achieve an acceptance criteria. The radiography system 100 comprises a controller 120 coupled to a screen or monitor (not shown). In the exemplary embodiment, the controller 120 is a computer console. An overall operation of the radiography system 100 is controlled by the controller 120. The screen or monitor (not shown) is used for displaying obtained images and related data. The acquired x-ray images or imager settings can be viewed or reviewed on the screen or monitor. The supporting device 110 has one or more wheels 1103 for mobility.

The radiation source 104 can be controlled via the controller 120 by a second operator 109. The second operator 109 may be a medical lab technician. An x-ray image acquisition may be run by releasing individual x-ray exposures for example by actuating a joy stick or a pedal or other suitable input means coupled to the controller 120. Actuation may result in a single or series of exposures acquired with predetermined tube positions. Repeated exposures acquired over a period of time may follow dynamic processes within the object. Repeated exposures acquired over a range of view angles can be used to obtain the 3D internal structure of the object 101 by a method of tomographic reconstruction. In the exemplary embodiment, the object 101 (such as a patient) is half lying in an examination bed 102 as shown in FIG. 1. The object 101 is in receipt of a field-of-view 103 that projects from the radiation source 104 to the detector 105. The object 101 (such as a patient) also may lie down in a horizontal position, and also may be at an oblique or even vertical angle, depending on the type of images that need to be obtained.

The radiation source 104 is coupled to the supporting device 110. The radiation source 104 is located in a first side of the object 101 for generating the plurality of beams 1041 toward the object 101. The detector 105 is located in a second side of the object 101 for detecting the plurality of beams 1041 from the radiation source 104. In some embodiments, the radiation source 104 and the detector 105 are located at opposite sides of the object 101 and the detector 105 is configured to receive beams 104 generated from the radiation source 104 and passing through the object 101. In the exemplary embodiment, the radiation source 104 is in front of the object 101 and the detector 105 is located behind the object 101. The radiography system 100 comprises a first sensor 115 also located in the first side of the object 101 for obtaining object related information. The radiography system 100 comprises at least one second sensor 118 disposed on the detector 105 for obtaining a detector-position related information. The controller 120 is coupled to the radiation source 104. The controller 120 is configured to reconstruct a 3D scene based on the object related information obtained by the first sensor 115 and the detector-position related information obtained by the second sensor 118. An operation of the radiography system 100 can be controlled by the second operator 109 based on the reconstructed 3D scene.

The first sensor 115 may be coupled to the radiation source 104, and it may be mounted to the radiation source 104 or the supporting device 110. In the exemplary embodiment, the first sensor 115 is mounted to the vertical column 1102 of the supporting device 110. The first sensor 115 comprises at least one of a camera and a range finder. The camera may be different kinds of cameras that can provide a stream of RGB images. The range finder may be a light detection and ranging device (LIDAR device). The range finder can provide a stream of point-cloud, depth sensing data. In the exemplary embodiment, the first sensor 115 may be a stereo camera 115 placed in an elevated position on the vertical column 1102. A position of the first sensor 115 on the vertical column 1102 can be adjusted. A field of view of the first sensor 115 spans a solid angle. The object 101, the detector 105 and a first operator 106 are all in the field of view of the first sensor 115. The first operator 106 may be a medical lab technician or a nurse for guiding the object 101 to a suitable position, such as lying on the examination bed 102. The detector 105 may be positioned into a suitable position behind the object 101 by the first operator 106. The first operator 106 maybe the same person with the second operator 109, or maybe two different people.

The radiography system 100 comprises at least one marker 117 placed on at least one of the object 101 and the first operator 106. In some embodiments, the at least one marker 117 comprises a first marker 1171 and a second marker 1172. The first marker 1171 is placed on the object 101. The second marker 1172 is placed on the first operator 106 for identifying the object 101 and the first operator 106. The first marker 1171 placed on the object 101 can also be used to determine a position of the object 101. The second marker 1172 placed on the first operator 106 can also be used to determine a position of the first operator 106. The marker 1171 placed on the object 101 and the marker 1172 placed on the first operator 106 can be seen in a frame captured by the first sensor 115. Thus, it can be easy to identify the object 101 and the first operator 106, and track positions of the object 101 and the first operator 106.

The at least one second sensor 118 placed on the detector 105 may be different type sensors. The at least one second sensor may comprise at least one of an inertial sensor, an electromagnetic sensor, and a proximity sensor. The number of the at least one second sensor disposed on the detector 105 is not limited, and it depends on working requirements.

In one embodiment, the at least one second sensor 118 comprises three inertial sensors. The inertial sensors are used for tracking a detector motion relative to the radiation source 104. Thus, a detector position can be directly determined by the inertial sensors placed on the detector 105.

In another embodiment, the at least one second sensor 118 comprises three electromagnetic sensors, and the at least one marker 1171 placed on the object 101 is an electromagnetic marker. The at least one marker 1171 can send out an electromagnetic signal that is picked up by the at least one second sensor 118. The at least one second sensor 118 can cooperate with the at least one marker 1171 to acquire a distance between the detector 105 and the at least one marker 1171. According to an additional relative position information pertaining to a location of the at least one marker 1171 placed on the object 101 in the camera video frames captured by the first sensor 115, the detector position is determined based on the distance and the relative position information between the at least one marker 1171 and the radiation source 104 acquired by the first sensor 115.

In another embodiment, the at least one second sensor 118 comprises three proximity sensors, and is sensitive to proximity to the object 101. The detector 105 may be placed on different positions relative to the object 101. Firstly, the detector 105 may be placed at a detector preliminary position at an edge of the object 101. Then, the detector 105 may be placed at a detector final position behind the object 101. The at least one second sensor 118 can acquire a relative position information of the detector 105 between the detector preliminary position at an edge of the object 101 and a detector final position behind the object 101. The detector position is determined based on a detector preliminary position obtained by the first sensor 115 and the relative positon information of the detector 105 between the detector preliminary position and the detector final position behind the object 101.

The radiography system 100 comprises an indicator 107 for providing an indication about how to align the radiation source 104, the detector 105 and the object 101. The indicator 107 can be inspected by the first operator 106 to adjust the position of at least one of the radiation source 104, the detector 105 and the object 101. The indicator 107 may be disposed on the radiation source 104 or the supporting device 110. The indicator 107 may be a voice prompt or a LED with red or green hue to indicate whether an acceptance criteria have been met. The indicator 107 can give an indication to the first operator 106 to adjust a position and/or a direction of at least one of the detector 105 and the object 101. For example, the indicator 107 may include five LEDs, one in a central position indicating whether an acceptance criteria has been met and four in surrounding positions indicating the direction of adjustment required to meet the acceptance criteria.

The radiography system 100 comprises a display device 113 disposed on the radiation source 104 for receiving data from the first sensor 115, the second sensor 118 and the controller 120. The display device 113 is used for indicating a relative displacement of an object anatomical centering position relative to a field-of-view 103 of the radiation source 104. The display device 113 is placed on the back of the radiation source 104. The display device 113 can show a real-time display output for assisting the second operator 109 to align system components with the object (the patient body parts) 101, including displacements and angles of target anatomy relative to an axis of the radiation source 104 and the detector 105. Therefore, the second operator 109 can adjust the radiation source 104 to align the radiation source 104 to the detector 105 and the object 101.

The controller 120 comprises an instruction module that is capable of giving the second operator 109 or the first operator 106 instructions to align the radiation source 104 with the detector 105, such as vocal or visual instructions showing moving up, down, closer and adjusting orientation, etc. to make sure that the orientation of the radiation source 104 is aligned to the orientation of the detector 105, the radiation source 104 is aligned to the center of the detector 105, and/or a distance between the radiation source 104 and the detector 105 is within a predetermined range. The vocal instructions or visual instructions are given to the first operator 106 or the second operator 109 through the indicator 107.

The controller 120 has a predetermined simultaneous localization and mapping (SLAM) algorithm. The controller 120 is configured to reconstruct a 3D scene based on the object related information obtained by the first sensor 115 and the detector-position related information obtained by the second sensor 118. The controller 120 can control an operation of the radiography system 100 based on the reconstructed 3D scene. The controller 120 is configured to obtain 3D scene information comprising at least one of an object 3D image information, an object positon related information, a detector-position related information, and a radiation source position related information based on the reconstructed 3D scene by the SLAM algorithm. Subsequently, meta-data such as a patient size, patient physiognomy, a patient thickness and an anatomical centering position relative to the field-of-view of the radiation source is extracted from the reconstructed dynamic 3D scene. Meta-data is used to optimize the radiation source exposure parameters, exposure timing and the image data processing after the radiation source exposure.

The radiation source 104 and the detector 105 may be aligned by the operator in two ways. In a first way, the detector 105 may be placed behind the object 101 by the first operator 106 and then the radiation source 104 may be moved towards the detector 105. Movement of the radiation source 104 may be accompanied by the adjustment of the collimated field-of-view 103. When moving the radiation source, the visual instructions or the vocal instructions may be given to the second operator 109 to guide the radiation source 104 movement. In an alternative embodiment, the source movement is actuated automatically to reach an acceptance criteria by a motor drive mechanism (not shown) contained within the source 104. In a second way, the radiation source 104 may be moved toward the object 101 by the second operator 109 to make sure the plurality of x-ray beams 1041 may cover the entire region of interest of the object 101. Then the detector 105 may be moved by the first operator 106 and be placed behind the object 101. During that, the visual instructions or the vocal instructions may be given to guide the first operator 106 to move the detector 105 and make the central x-ray from the radiation source 104 pass through the detector center. According to some embodiments of this disclosure, the real-time alignment status of the radiation source 104 and the detector 105 relative to the object 101 may be acquired by the second operator 109. The detector position, the object position and/or the radiation source position may be correspondingly adjusted by the operator based on the real-time reconstructed 3D scene.

According to one embodiment, controlled operation of the radiography system comprises adjusting a position and/or a direction of the radiography source 104, adjusting a position and/or a direction of the detector 105, and/or optimizing at least one of the exposure parameters of the radiation source. Adjusting the position and/or the direction of the at least one the radiation source 104, the object 101 and the detector 105 may comprise aligning the radiation source 104 and the detector 105 relative to the object 101. The radiation source 104 may be aligned with a center area of the detector 105 to make an interested area of the object 101 to be scanned in the field-of-view 103 of the radiation source 104. Optimizing at least one of the exposure parameters of the radiation source 104 comprises adjusting at least one of an operation voltage of the radiation source, an exposure time, and an exposure dosage. The operation voltage of the radiation source can be set in response to a patient's physiognomy, in particular a patient thickness as evidenced by depth information in the object 3D image information. In other words, the operation voltage of the radiation source is adjusted to vary directly with the patient's thickness. For example, a precomputed look-up table that associates the operation voltage with the patient thickness may be used.

Figure 2:
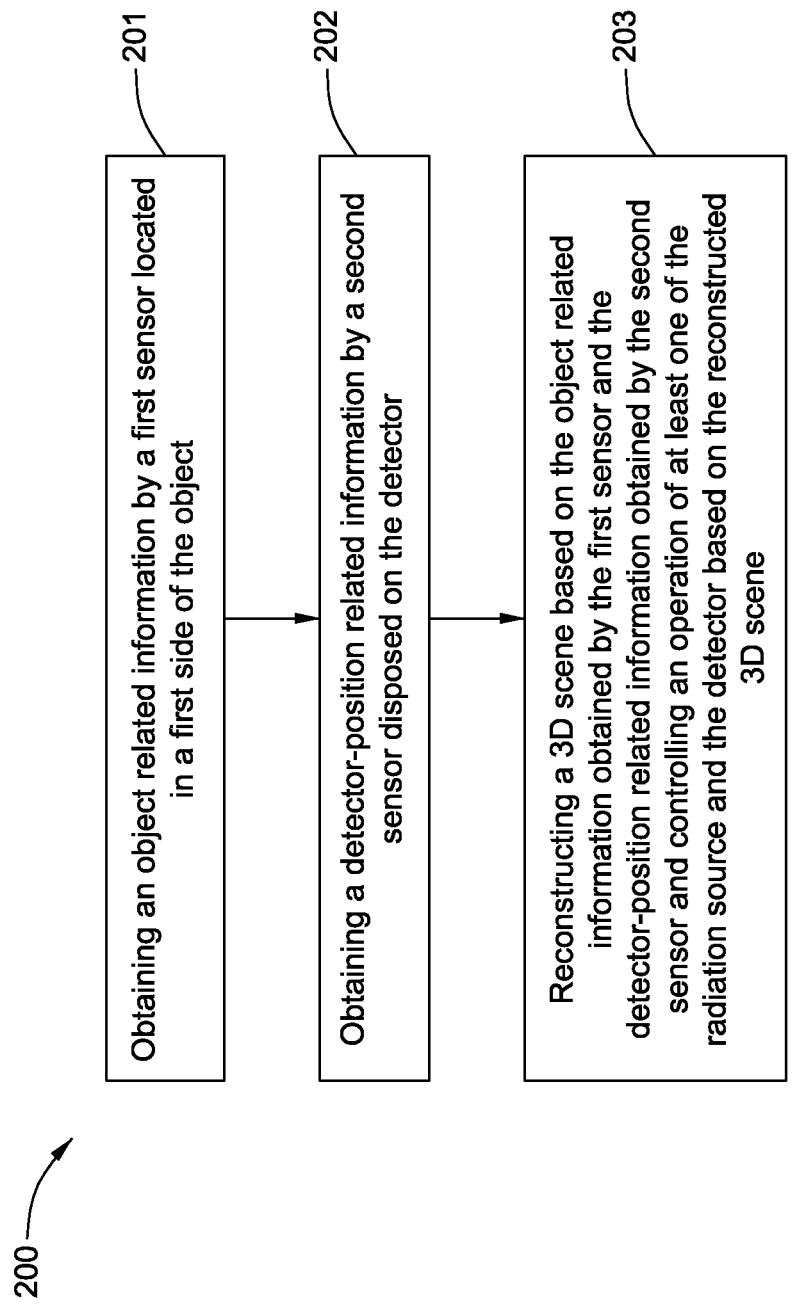
FIG. 2 shows an exemplary workflow used to control a radiography system, in accordance with an embodiment of the present disclosure.

The present disclosure also provides a method of controlling a radiography system for imaging an object. FIG. 2 illustrates an exemplary workflow of a method 200 to control a radiography system in accordance with an embodiment of the present disclosure, wherein the method 200 of controlling the radiography system comprises: step 201 of obtaining an object related information by a first sensor 115 located in a first side of the object 101; step 202 of obtaining a detector-position related information by a second sensor 118 disposed on the detector 105; step 203 of reconstructing a 3D scene based on the object related information obtained by the first sensor 115 and the detector-position related information obtained by the second sensor 118 and controlling an operation of the at least one of the radiation source 104 and the detector 105 based on the reconstructed 3D scene.

Figure 3:
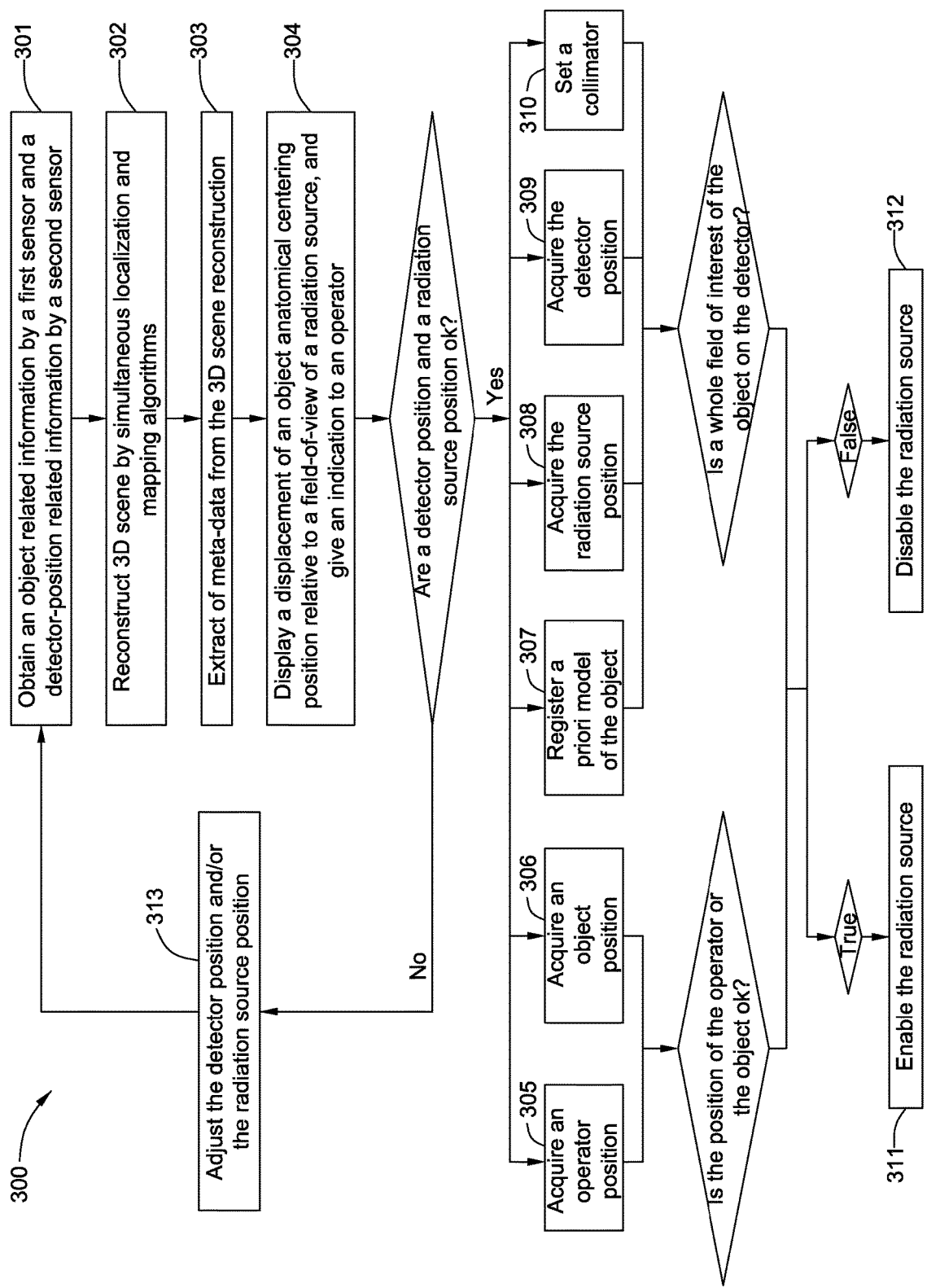
FIG. 3 illustrates an exemplary process for controlling a radiography system, in accordance with an embodiment of the present disclosure.

FIG. 3 is a flow chart illustrating in detail an exemplary process 300 of controlling a radiography system like the radiography system 100. In the process, an actuation of exposure is prevented unless two conditions are met: wherein the first condition is that the operator is in a safe place and the second condition is that the whole field of interest is projected by the radiation source on the detector active area. At step 301, the real-time object related information is obtained by the first sensor 115 and the real-time detector-position related information is obtained by the second sensor 118. At step 302, a 3D scene is reconstructed by the simultaneous localization and mapping algorithm pre-set in the controller 120. At step 303, a meta-data is extracted from the reconstructed 3D scene by the controller 120. At step 304, a real-time displacement of an object anatomical centering position relative to the field-of-view of the radiation source 104 is displayed by the display device 113. An indication may be given to the operator to adjust the detector position or adjust the radiation source 104. Through the step 304, the real-time alignment status of the detector 105 and the radiation source 104 relative to the object 101 are acquired by the operator. Thus, a corresponding adjustment of the detector 105 and/or the radiation source 104 may be made by the operator according to the vocal instructions or the visual instructions given by the indicator 107.

A judgement is made by the operator based on the step 304 if that a detector position and a radiation source position shown on the display device 113 are both ok? If the detector position and the radiation source position are both ok, then move to next stage steps. The next stage steps include a first step group and a second step group. The first step group comprises step 305 and step 306. At step 305, the operator position is acquired. At step 306, the object position is acquired. The second step group comprises step 307 to step 310. At step 307, a priori model of the object (for example a patient atlas registration and scaling model) is pre-registered. At step 308, the radiation source position is acquired. At step 309, the detector position is acquired. At step 310, parameters of a collimator (not shown) is set.

Based on the first step group of step 306 and step 307, a judgement is made by the operator if that the positions of the operator and the object are ok. In the exemplary embodiment, the position of the operator is ok when the first operator 106 moves to a safe location, for example, outside the examination room. The position of the object 101 is ok means that the object is in a suitable position in the examination room. Based on the second group step of step 307 to step 310, a judgement is made by the operator if that a whole field of interest of the object is on the detector 105. If the positions of the operator and the object are ok and the whole field of interest of the object is on the detector 105, a "True" instruction is given to the second operator 109 by the controller 120 through an "AND" logical gate. If the position of either the operator or the object is not ok or if not the whole field of interest of the object is on the detector 105, a "False" instruction is given to the second operator 109. If the "True" instruction is given to the second operator 109, a step 311 is executed to enable the radiation source 104. If the "False" instruction is given to the second operator 109, a step 312 is executed to disable the radiation source 104 to prevent unnecessary exposure delivered to the object 101.

If the object anatomical centering position shown on the display device 113 is not in the center of the field-of-view of the radiation source 104, after the step 304, an indication that the detector and/or the radiation source are not in the suitable position may be given to the second operator 109. Then, a step 313 is executed to adjust the detector position and/or the radiation source position. Then the steps 301 to 304 may be repeated until the object anatomical centering position shown on the display device 113 is in the center of the field-of-view of the radiation source 104, i.e., the detector and the radiation source are in the suitable positions.

In the radiography system 100, the position of the radiation source 104 and/or the position of the detector 105 may be adjusted by the operator or the drive mechanism based on the continuous and dynamic 3D scene reconstruction. Thus, the radiation source 104 and the detector 105 can be easily aligned to the object anatomical centering position by the operator. The exposure dosage may be optimized according to the object 3D image. In other words, a lower radiation dose can be delivered to the patient and the operators by optimizing the exposure parameters and the acquisition timing during the examination process. In this disclosure, the radiography system 100 is actuated/enabled until the two conditions as discussed above are met. It can prevent an unacceptable rate of retakes, a long examination time and potential excess exposure dose delivered to the patients and the operators.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A radiography system for imaging an object, comprising:
   a radiation source located in a first side of the object, for generating a plurality of beams;
   a detector located in a second side of the object, for detecting the plurality of beams from the radiation source;
   a first sensor located in the first side of the object, for obtaining an object related information;
   a second sensor disposed on the detector for obtaining a detector-position related information; and
   a controller configured to reconstruct a 3D scene based on the object related information obtained by the first sensor and the detector-position related information obtained by the second sensor and control operation of at least one of the radiation source and the detector based on the reconstructed 3D scene.

2. The radiography system of claim 1, wherein the operation of at least one of the radiation source and the detector comprises adjusting a position and/or a direction of at least one of the radiation source and the detector, and/or optimizing at least one of the exposure parameters of the radiation source.

3. The radiography system of claim 1, wherein the controller is configured to obtain 3D scene information comprising at least one of an object 3D image information, an object positon related information, a detector-position related information, and a radiation source position related information based on the reconstructed 3D scene and control the operation of the radiation source and the detector based on the 3D scene information.

4. The radiography system of claim 1, comprising a supporting device for supporting and articulating the radiation source, wherein the supporting device comprises a transport frame and a vertical column mounted on the transport frame, the radiation source is coupled to the vertical column, and the first sensor is mounted on the vertical column or on the radiation source.

5. The radiography system of claim 4, comprising an indicator disposed on the radiation source or the supporting device to provide an indication to adjust a position and/or a direction of at least one of the radiation source, the detector and the object.

6. The radiography system of claim 1, comprising a display device disposed on the radiation source to indicate a relative displacement of an object anatomical centering position relative to a field-of-view of the radiation source.

7. The radiography system of claim 1, wherein the first sensor comprises at least one of a camera and a range finder.

8. The radiography system of claim 1, wherein the second sensor comprises an inertial sensor for tracking a detector motion relative to the radiation source to determine a detector position.

9. The radiography system of claim 1, comprising at least one marker placed on at least one of the object and an operator for identifying the object and the operator or determining the position of the object and/or the operator.

10. The radiography system of claim 9, wherein the at least one marker is an electromagnetic coil.

11. The radiography system of claim 10, wherein the at least one marker is placed on the object, and the second sensor comprises at least one electromagnetic sensor cooperating with the at least one marker to acquire a distance between the detector and the at least one marker, and a detector position is determined based on the distance and a relative position information between the at least one marker and the radiation source acquired by the first sensor.

12. The radiography system of claim 1, wherein the second sensor is a proximity sensor to acquire a relative position information of the detector between a detector preliminary position at an edge of the object and a detector final position behind the object.

13. The radiography system of claim 12, wherein a detector position is determined based on a detector preliminary position obtained by the first sensor and the relative positon information of the detector.

14. A method of controlling a radiography system comprising a radiation source and a detector for imaging an object, comprising:
    obtaining an object related information by a first sensor located in a first side of the object;
    obtaining a detector-position related information by a second sensor disposed on the detector; and
    reconstructing a 3D scene based on the object related information obtained by the first sensor and the detector-position related information obtained by the second sensor and controlling an operation of at least one of the radiation source and the detector based on the reconstructed 3D scene.

15. The method of claim 14, wherein the operation of the at least one of the radiation source and the detector comprising adjusting a position and/or a direction of at least one of the radiation source and the detector, and/or optimizing at least one of an exposure parameter of the radiation source.

16. The method of claim 14, comprising obtaining 3D scene information comprising at least one of a detected object 3D image information, a detected object positon related information or the detector-position related information, and a radiation source position related information based on the reconstructed 3D scene, wherein the operation of the radiography system is controlled based on the 3D scene information.

17. The method of claim 14, comprising providing an indication to adjust a position and/or a direction of at least one of the radiation source, or the detector or the detected object by an indicator.

18. The method of claim 14, wherein the second sensor comprises an inertial sensor for tracking a detector motion relative to the radiation source, and the detector-position related information comprises a detector position information obtained by the inertial sensor.

19. The method of claim 14, wherein the second sensor comprises an electromagnetic sensor, and the detector-position related information comprises a relative position information between the detector and a surface of the object obtained by the electromagnetic sensor.

20. The method of claim 14, wherein the second sensor comprises a proximity sensor, and the detector-position related information comprises a relative position information of the detector between a detector preliminary position at an edge of the object and a detector final position behind the object obtained by the proximity sensor.

* * * * *